United States Patent [19]

Leon Leon

[11] Patent Number: 4,883,663
[45] Date of Patent: Nov. 28, 1989

[54] THERAPEUTIC POWDER AND PROCESS OF MANUFACTURING

[76] Inventor: Rogue O. Leon Leon, Buenavista No. 46, Col., Lindavista, Mexico, D.F. 07300

[21] Appl. No.: 94,615

[22] Filed: Sep. 9, 1987

[30] Foreign Application Priority Data

Sep. 9, 1986 [MX] Mexico .................................. 298

[51] Int. Cl.$^4$ ............................................. A61L 35/78
[52] U.S. Cl. .................................................. 424/195.1
[58] Field of Search ...................................... 424/195.1

Primary Examiner—Mark L. Bell
Attorney, Agent, or Firm—Lane and Aitken

[57] ABSTRACT

A therapeutic powder is manufactured from the bark and outer layer of sap wood from the tree, Mimosa Tenuiflora poir. The bark and wood is chemically and manually washed, then roasted to separate the curative active ingredients from the cells containing the active ingredients, and then ground into the powder of the invention. The ground powder is then sterilized. The powder is therapeutic when applied to burns, wounds, lesions and other skin injuries.

10 Claims, No Drawings

THERAPEUTIC POWDER AND PROCESS OF MANUFACTURING

This invention relates to a method of manufacturing a powder useful in the treatment of burns, wounds, lesions, etc., and also as a cosmetic or toiletry, and to the powder made by the method.

SUMMARY OF THE INVENTION

The powder of the present invention is made from a wood product obtained from a Mimosa tree, and in particular the species of the Mimosa tree known scientifically as the Mimosa Tenuiflora poir. The wood product comprises the bark and/or the adjacent layer of wood, which strips off with the bark when the bark is stripped from the tree. The wood product is processed into the powder by first chemically cleaning the bark and wood, roasting the bark and wood, grinding the roasted wood to powder, and then sterilizing the resulting powder. The resulting powder, when applied directly to a burn, wound, lesion or other similar type injury, acts as an anesthetic, prevents infection and aids in the healing process by promoting skin growth. In addition the scarring caused by the injury is greatly reduced or eliminated.

Accordingly, an object of the present invention is to provide an improved therapeutic powder for topical treatment of skin injuries such as burns, wounds, lesions, etc.

Another object of the present invention is to provide a method of processing wood material having curative properties into a therapeutic powder for the topical treatment of skin injuries such as burns, wounds, lesions, etc.

DESCRIPTION OF PREFERRED EMBODIMENTS

In accordance with the present invention, the bark is stripped from a Mimosa tree, which preferably a species of a Mimosa tree known as scientifically as the Mimosa Tenuiflora poir. When the bark is stripped from the tree, an outer layer of sapwood will be stripped from the tree with the bark. It has been discovered that the bark of this species of Mimosa tree, and the outer layer of wood which strips from the tree with the bark, when properly processed, have remarkable curative properties. In accordance with the invention the bark and wood layer are processed by washing the bark and wood in an oxidizer and germicide such as an aqueous solution of 0.1-1.4% by weight of chlorine dioxide with the preferred solution being 0.1% chlorine dioxide by weight. The washing step is carried out by immersing the bark and wood in the solution for a period of at least one half hour while providing moderate agitation to the solution. The washing step may be carried out at room temperature. The washing step eliminates irritating substances and pyrogens from the wood product. Following the washing step, most of the cleansing solution is eliminated from the bark and wood by spin drying the bark and wood. After the drying, which is carried out at room temperature, the bark and wood are roasted by heating the material to an elevated temperature in an atmosphere of air. The roasting temperature may be anywhere from 60 degrees centigrade to 250 degrees centigrade, but preferably is in the range of 80 degrees centigrade to 140 degrees centigrade. The optimal roasting temperature is 125 degrees centigrade. The wood and bark is roasted for a period of time sufficient for an effective amount of the curative active ingredients in the material to separate from the cells containing the active ingredients as determined by the wood turning sustantially darker brown, but without any carbonization of the wood or wood materials. When the roasting temperature is at the optimal value of 125 degrees centigrade, the roasting time is from 15 minutes to one hour in duration.

After roasting of the bark and wood is completed, the material is ground into a powder made up of particles no larger than 1 mm. in diameter and preferably having a particle size such that at least 90% of the particles are small enough to pass through 100 mesh (U.S. sieve) screen. A powder in which the particles will pass through a 100 mesh screen is referred to as minus 100 mesh powder. To achieve a minus 100 mesh powder, the powder resulting from the grinding operation is vibrated over a 100 mesh screen. The particles that pass through the screen are collected as the powder of the invention. The final step in the processing is sterilizing the powder. This step preferably is effected by contacting the powder with a sterilizing gas, such as ethylene oxide.

To use the powder, the powder is simply applied topically to a burn, wound, lesion or other skin injury. The powder is particularly effective when applied to second degree burns. When the powder has been applied, it has a strong anesthetic affect, prevents infection of the injury, increases the rate of healing of the injury by promoting skin growth, and greatly reduces or eliminates scarring from the injury.

Instead using the powder by applying the powder directly to the injury, the powder or an extract of the powder may be used in a cosmetic base or other medicine. The powder or an extract of the powder can also be used in cosmetics or toiletries, or edible materials such as gum.

The curative properties of the powder come from both the bark and the outer layer of wood which strips away with the bark. Accordingly, the powder may be made exclusively either just from the bark or from this outer layer of wood which strips away from the tree with the bark. The remarkable curative properties from the powder have been achieved with the wood material from the species of Mimosa, Mimosa Tenuiflora poir. It is believed that these curative properties, to some degree, will also be obtained from the bark and outer layer of wood taken from other species of Mimosa trees.

The above description is of a preferred embodiment of the invention and modification may be made thereto, without departing from the spirit of the invention, which is defined in the appended claims.

I claim:

1. A method of manufacturing a therapeutic powder for treatment of skin injuries comprising the steps of:
   providing a wood material selected from the group consisting of the bark of a Mimosa tree, the outer layer of wood of the Mimosa tree that is stripped away from the tree with the bark of the tree, and a mixture of said bark and said wood, roasting said wood material for a time and temperature sufficient for curative active ingredients in said wood material to separate from the cells containing said active ingredients, and grinding said wood material into a powder.

2. A method as recited in claim 1, wherein said mimosa tree is the species of mimosa tenuiflora poir.

3. A method as recited in claim 1, further comprising the step of washing said wood material prior to said step of roasting to remove irritants from said wood product.

4. A method as recited in claim 3, wherein said washing step comprises immersing said wood product in an aqueous solution including 0.1–1.4% chlorine dioxide by weight.

5. A method as recited in claim 1, wherein said roasting step is carried out at a temperature in the range of 60 degrees centigrade and 250 degrees centigrade.

6. A method as recited in claim 1, wherein said roasting step is carried out at a temperature range of 80 degrees centigrade to 140 degrees centigrade.

7. A method as recited in claim 1, wherein said roasting step is carried out at a temperature of about 125 degrees centigrade.

8. A therapeutic powder manufactured by the method of claim 1.

9. A powder as recited in claim 8 having a particle size of 1 mm in diameter or less.

10. A powder as recited in claim 8, wherein powder is minus 100 mesh powder.

* * * * *